US010537562B2

(12) United States Patent
Mehta et al.

(10) Patent No.: US 10,537,562 B2
(45) Date of Patent: Jan. 21, 2020

(54) DELAYED RELEASE PHARMACEUTICAL COMPOSITION OF PANTOPRAZOLE AND PROCESS FOR FORMULATION THEREOF

(71) Applicant: Jubilant Generics Limited, Noida, Uttar Pradesh (IN)

(72) Inventors: Kamal Surendrakumar Mehta, Noida (IN); Saurabh Srivastava, Noida (IN); Dinesh Kumar, Noida (IN); Amit Kumar Jha, Noida (IN); Subash Chandra Mohanta, Noida (IN); Sunil Kumar Panda, Noida (IN); Ganesh Vinayak Gat, Noida (IN)

(73) Assignee: Jubilant Generics Limited (IN)

( * ) Notice: Subject to any disclaimer, the term of this patent is extended or adjusted under 35 U.S.C. 154(b) by 0 days.

(21) Appl. No.: 16/087,043

(22) PCT Filed: Oct. 6, 2017

(86) PCT No.: PCT/IB2017/056182
§ 371 (c)(1),
(2) Date: Sep. 20, 2018

(87) PCT Pub. No.: WO2018/065952
PCT Pub. Date: Apr. 12, 2018

(65) Prior Publication Data
US 2019/0099408 A1     Apr. 4, 2019

(30) Foreign Application Priority Data

Oct. 6, 2016   (IN) .............................. 201611034271

(51) Int. Cl.
| | | |
|---|---|---|
| *A61K 31/4439* | (2006.01) | |
| *A61K 9/00* | (2006.01) | |
| *A61K 9/50* | (2006.01) | |
| *A61P 1/04* | (2006.01) | |
| *A61K 47/10* | (2017.01) | |
| *A61K 47/20* | (2006.01) | |
| *A61K 47/38* | (2006.01) | |

(52) U.S. Cl.
CPC ........ *A61K 31/4439* (2013.01); *A61K 9/0095* (2013.01); *A61K 9/5047* (2013.01); *A61K 9/5073* (2013.01); *A61K 9/5089* (2013.01); *A61K 47/10* (2013.01); *A61K 47/20* (2013.01); *A61K 47/38* (2013.01); *A61P 1/04* (2018.01); *A61K 9/5026* (2013.01)

(58) Field of Classification Search
CPC .. A61K 9/0095; A61K 9/5047; A61K 9/5073; A61K 9/5089; A61K 47/10; A61K 47/20; A61K 47/38; A61K 9/5026; A61K 31/4439; A61P 1/04
See application file for complete search history.

(56) References Cited

U.S. PATENT DOCUMENTS

| | | | |
|---|---|---|---|
| 7,544,370 B2 * | 6/2009 | Venkata Ramana Rao ................. | A61K 9/0095 424/456 |
| 7,550,153 B2 * | 6/2009 | Venkata Ramana Rao ................. | A61K 9/0095 424/456 |
| 7,553,498 B2 * | 6/2009 | Venkata Ramana Rao ................. | A61K 9/0095 424/456 |
| 7,838,027 B2 * | 11/2010 | Venkata Ramana Rao ................. | A61K 9/0095 424/456 |
| 8,865,212 B2 * | 10/2014 | Ghosh .................... | A61K 31/44 424/465 |
| 2003/0180352 A1 * | 9/2003 | Patel .................... | A61K 9/1617 424/465 |
| 2005/0129761 A1 * | 6/2005 | Venkata Ramana Rao ................. | A61K 9/0095 424/470 |
| 2007/0042033 A1 * | 2/2007 | Venkata Ramana Rao ................. | A61K 9/0095 424/451 |
| 2007/0196443 A1 * | 8/2007 | Ramana Rao ....... | A61K 9/0095 424/439 |
| 2007/0196444 A1 * | 8/2007 | Ramana Rao ....... | A61K 9/0095 424/439 |
| 2009/0022795 A1 * | 1/2009 | Ghosh .................. | A61K 9/2886 424/465 |
| 2009/0263475 A1 * | 10/2009 | Manne ................... | A61K 9/145 424/451 |
| 2010/0297226 A1 * | 11/2010 | Penhasi ................ | A61K 9/2077 424/465 |

(Continued)

OTHER PUBLICATIONS

Das et al. "Delayed Release Formulation of Pantoprazole Using Sureteric Aqueous Dispersion System," Scholars Research Library, Der Pharmacia Lettre, 2013, 5(5):175-186.*

*Primary Examiner* — Blessing M Fubara
(74) *Attorney, Agent, or Firm* — William D. Hare, Esq.; McNeely, Hare & War, LLP

(57) ABSTRACT

The present invention discloses stable delayed release multiparticulate powder for oral suspension of proton pump inhibitor compounds comprising: a) a core with an effective amount of proton pump inhibitor and at least one or more pharmaceutical excipients, b) at least one water-soluble seal coating over core c) at least one enteric coating layer over the seal coat wherein the said core comprises disintegrant (0-10%) and/or surfactant (0-2%) w/w of core. The prior art discloses restrictive formulation technique and suggest high amount of various excipients to achieve desired technical attributes. The prepared test formulations exhibited desired pharmaceutical technical attributes like drug release, assay, stability, no polymorphic change, reduced sticking to nasogastric and gastronomy tubes, and packaging material.

19 Claims, 2 Drawing Sheets

(56) References Cited

U.S. PATENT DOCUMENTS

| | | | |
|---|---|---|---|
| 2012/0231073 A1* | 9/2012 | Manne | A61K 9/145 424/457 |
| 2014/0147500 A1* | 5/2014 | Fallon | A61K 38/465 424/468 |
| 2014/0314846 A1* | 10/2014 | Penhasi | A61K 9/2077 424/465 |

* cited by examiner

DELAYED RELEASE PHARMACEUTICAL COMPOSITION OF PANTOPRAZOLE AND PROCESS FOR FORMULATION THEREOF

FIELD OF THE INVENTION

This invention in general relates to stable pharmaceutical composition comprising acid labile compounds or their pharmaceutically acceptable salts, esters, solvates, polymorphs, enantiomers or mixtures thereof. In particular, the present invention discloses a stable solid oral delayed release multiparticulate pharmaceutical composition comprising benzimidazole derivatives and process for preparing the same.

BACKGROUND OF THE INVENTION

Proton pump inhibitors (PPIs) are agents having powerful inhibitory action against H+/K+-adenosine triphosphate (ATP) and prevent secretion of gastric acid. For example, Pantoprazole sodium is a proton pump inhibitor and is pharmaceutically used in short-term treatment (7 to 10 days) of Gastroesophageal Reflux Disease (GERD) associated with a history of erosive esophagitis as well as for the treatment of pathological hypersecretory conditions including Zollinger-Ellison Syndrome in adults. These Proton pump inhibitors are generally reported to be acid labile compounds/derivatives.

Pantoprazole sodium, is a substituted benzimidazole derivative and is chemically known as sodium 5-(difluoromethoxy)-2-[[(3,4-dimethoxy-2-pyridinyl)methyl]sulfinyl]-1H benzimidazole. In various marketed formulations crystalline sesquihydrate polymorphic form is used. Sodium 5-(difluoromethoxy)-2-[[(3,4-dimethoxy-2-pyridinyl)methyl]sulfinyl]-1H benzimidazole sesquihydrate is represented by the following formula:

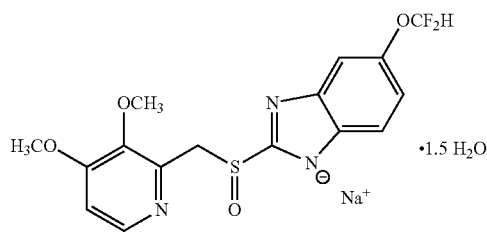

Following formulations of Pantoprazole sodium are approved in the USA:
(I) 20 & 40 mg delayed release tablets
(II) i.v. infusion formulation (Eq 40 mg base/vial)
(III) Delayed release granules for oral suspension (Eq 40 mg base)

Patent publication U.S. Pat. No. 4,758,579 is assigned to Nycomed which covers Pantoprazole as a product.

Pantoprazole sodium sesquihydrate delayed release granules for oral suspension are marketed in the USA under the brand name PROTONIX® and contain crospovidone, hypromellose, methacrylic acid copolymer, microcrystalline cellulose, polysorbate 80, povidone, sodium carbonate, sodium lauryl sulfate, talc, titanium dioxide, triethyl citrate, and yellow ferric oxide as the inactive ingredients. For patients having difficulty in swallowing, such as pediatric and geriatric patients, oral liquid formulations such as suspension is the preferred dosage form. Pantoprazole sodium sesquihydrate delayed release granules for oral suspension can be administered by sprinkling the granules on one teaspoonful of applesauce or empty granules into a small cup or teaspoon containing one teaspoon of apple juice and consume this within 10 minutes of preparation.

Patent publication U.S. Pat. No. 5,997,903 is assigned to Byk Gulden discloses oral delayed release tablet dosage forms of Pantoprazole.

Patent publication U.S. Pat. No. 8,865,212 is assigned to Jubilant Generics Ltd. discloses non-multiple unit pellet system (MUPS) of an acid labile benzimidazole derivative in tablet dosage forms devoid of disintegrant.

Patent publications U.S. Pat. Nos. 7,544,370, 7,550,153, 7,553,498 and 7,838,027 are assigned to Wyeth and listed in Approved Drug Products with Therapeutic Equivalence Evaluations (Orange Book) disclose multiparticulate formulation of Pantoprazole. As per the disclosure of these patent publications, the benzimidazole derivatives employed as proton pump inhibitors are easily destroyed in the acid milieu and thus are difficult to formulate for oral administration. These patent publications highlight various formulation challenges associated with multiparticulate formulation of Pantoprazole such as, stability issues at room temperature, inappropriate release under acid conditions and adherence to the intestinal walls, nasogastric and gastronomy tubes. As per these patent publications, the desired formulation was achieved by essentially using the following proportion of pharmaceutical excipients:

| Ingredients | Range | % w/w of the core |
|---|---|---|
| Pantoprazole sodium | about 45% | 45.24 |
| Microcrystalline cellulose | about 25 to 30% | 27.25 |
| Polysorbate 80 | about 4 to 6% | 5 |
| Crospovidone | about 14 to 16% | 15 |
| Hypromellose | about 0.5 to 2% | 1 |
| Sodium carbonate | about 5 to 8% | 6.5 |

Multiparticulate formulations of proton pump inhibitor are prepared by mixing disintegrant(s) and surfactant for consistent and satisfactory dissolution of drug from the dosage form. Disintegrants are often considered as most important, as they ensure the break-up of the dosage form into smaller fragments upon ingestion, to allow the onset of drug dissolution and eventual absorption. Disintegrants are often associated with promoting moisture penetration into the matrix of core of the dosage form to initiate the disintegration process. The disintegration process can mechanistically be subdivided into stages, breakdown into coarse aggregates and subsequent deaggregation into fine primary particles which subsequently increases the surface area.

Surfactants used in enteric coated dosage forms, provide better wettability and enhance the solubility of the drug, which improves the dissolution property. On the other hand, higher amount of surfactant can also cause gastric irritation. As per patent publication listed in Approved Drug Products with Therapeutic Equivalence Evaluations (Orange Book) by the innovator for the desired technical attributes, disintegrant is used in the range of 14-16% w/w and surfactant is used in the range of 4-6% w/w, which is very high.

Surprisingly, it is found by the inventors of the present invention that multiparticulate compositions of benzimidazole compounds, particularly Pantoprazole compositions, can be prepared by varying the amount of essential excipients like disintegrant and surfactant. Further, by avoiding the higher amount of disintegrant and/or using lesser amount of surfactant desired pharmaceutical technical attributes were achieved like drug release, assay, stability, no polymorphic change, reduced or no sticking to nasogastric and gastronomy tubes, and packaging material.

SUMMARY OF THE INVENTION

The present invention relates to a stable solid oral delayed release multiparticulate pharmaceutical composition prepared by varying the amount of essential excipients like disintegrant and/or surfactant, which exhibited desired pharmaceutical technical attribute comparable to the innovator's marketed product (PROTONIX® suspension). Preferably, by avoiding the higher amount of disintegrant and/or using lesser amount of surfactant, desired pharmaceutical technical attributes were achieved like drug release, assay, stability, no polymorphic change, reduced or no sticking to nasogastric and gastronomy tubes, and packaging material.

DESCRIPTION OF THE INVENTION

Figure 1:
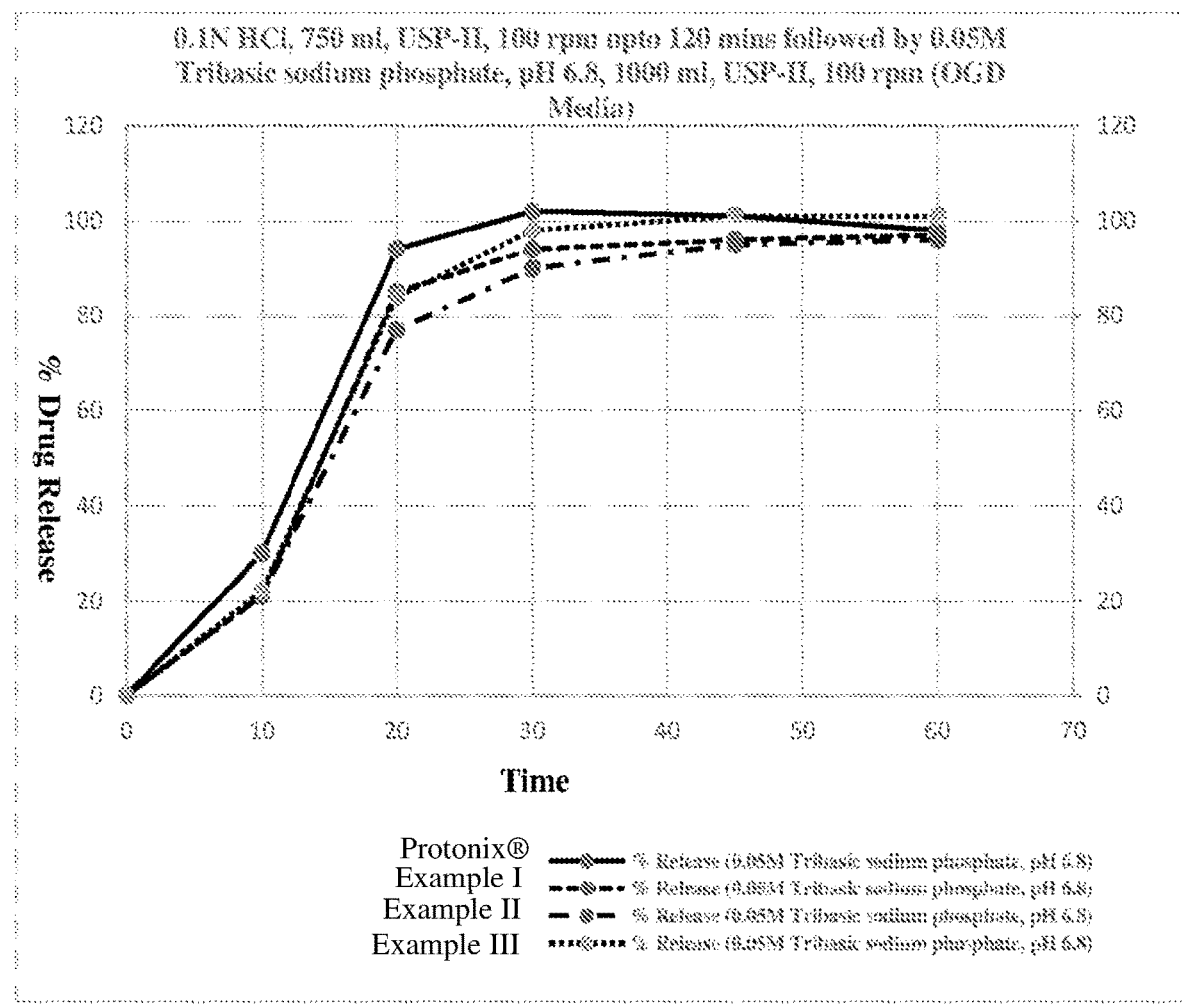
FIG. 1 is a graphical depiction of % drug release (dissolution profile) of commercially available Pantoprazole delayed release powder for oral suspension "Protonix®" from Wyeth and Pantoprazole delayed release powder for oral suspension of example I-III.

The present invention can be more readily understood by reading the following detailed description of the invention and study of the included examples.

As used herein, the term "composition", as in pharmaceutical composition, is intended to encompass a drug product comprising Pantoprazole or its pharmaceutically acceptable salts, esters, solvates, polymorphs, enantiomers or mixtures thereof, and the other inert ingredient(s) (pharmaceutically acceptable excipients). Such pharmaceutical compositions are synonymous with "formulation" and "dosage form". Pharmaceutical composition of the invention include, but is not limited to, pellets, granules, beads, minitabs, spherules, beadlets, microcapsules, millispheres, microspheres and the like. Preferably, the pharmaceutical composition refers to spheres. More preferably, the pharmaceutical composition refers to delayed release pellets/spheres for oral suspension, wherein granules and powders for oral suspension are alike. The term "multiparticulate" means a plurality of discrete or aggregated particles, pellets, beads, spheres or spheroids or mixture thereof, irrespective of their size, shape or morphology. Each individual particle, pellet, bead, spheres or spheroids making up a multiparticulate is referred to herein, as a "particulate." Preferably the multiparticulates are spheroids prepared by extrusion spheronization.

"Acid labile benzimidazole" as used herein refers to benzimidazole compounds of therapeutic interest whose half-life is less than 10 minutes in an aqueous solution, that has a pH less than 4, for example Pantoprazole, Lansoprazole, Rabeprazole, Omeprazole, Timoprazole, Picoprazole and the like.

"Pantoprazole" as used herein refers to the free acid form, its salts, esters, solvates, polymorphs, enantiomers or mixtures thereof. Preferably, the salt of Pantoprazole used here is Pantoprazole sodium. More preferably, the salt of Pantoprazole used here is Pantoprazole sodium sesquihydrate.

The term "core" as used herein refers to pellets/spheres comprising a drug, at least a diluent, an alkaline agent, wherein the core also comprises a varying amount of disintegrant and/or surfactant.

The term "excipient" means a pharmacologically inactive component such as a diluent, lubricant, surfactant, carrier, or the like. The excipients that are useful in preparing a pharmaceutical composition are generally safe, non-toxic and are acceptable for veterinary as well as human pharmaceutical use. Reference to an excipient includes both one and more than one such excipient. Co-processed excipients are also covered under the scope of present invention. Further, excipient may be in the form of powders or in the form of dispersion. Combination of excipients performing the same function may also be used to achieve desired formulation characteristics.

"Delayed release" as used herein refers to a solid dosage, which releases a drug (or drugs) at a time other than promptly after administration. For the purpose of this invention enteric-coated articles are delayed release dosage forms.

The term "substantially free Surfactant" as used herein refers to the amount which is in range from 0-2% w/w by total weight of core.

The term "substantially free disintegrant" as used herein refers to 0-1% w/w by total weight of the core.

As used herein, the term "about" means±approximately 10% of the indicated value.

The term "w/w" as used herein refers the total weight of the core composition.

In another embodiment, the present invention includes a solid oral multiparticulate pharmaceutical composition comprising Pantoprazole or its pharmaceutically acceptable salts, esters, solvates, polymorphs, enantiomers or mixtures thereof.

In an another embodiment of the invention, the solid oral delayed release multiparticulate pharmaceutical composition comprises a pharmacologically effective amount of proton pump inhibitor, preferably Pantoprazole or its pharmaceutically acceptable salt, esters, solvates, polymorphs, enantiomers or mixtures thereof, wherein the composition is substantially free of disintegrant and/or surfactant.

In another embodiment of the invention, the delayed release multiparticulate powder for oral suspension comprising:
a) a core comprising an effective amount of Pantoprazole or its pharmaceutically acceptable salts, at least one diluent and an alkaline agent,
b) at least one seal coating layer over core
c) at least one enteric coating layer over the seal coat
d) and optionally an outer seal coating layer
wherein the said core is substantially free of disintegrant (0-1% w/w) and/or surfactant (0-2% w/w).

Yet another embodiment of the present invention, the delayed release multiparticulate powder for oral suspension prepared by extrusion spheronization process comprising:
a) a core comprising an effective amount of Pantoprazole or its pharmaceutically acceptable salts and at least one diluent and an alkaline agent,
b) at least one seal coating layer over core and
c) at least one enteric coating layer over the seal coat
wherein the said core comprises of disintegrant from 1-10% w/w and/or surfactant from 0-2% w/w.

In another embodiment of the invention, the delayed release multiparticulate powder for oral suspension prepared by extrusion spheronization process comprising:

a) a core comprising an effective amount of Pantoprazole or its pharmaceutically acceptable salts and at least one diluent and an alkaline agent,
b) at least one seal coating layer over core and
c) at least one enteric coating layer over the seal coat
wherein the said core comprises of disintegrant from 1-10% w/w and free of surfactant.

Yet another embodiment of the present invention, the delayed release multiparticulate powder for oral suspension of Pantoprazole or its pharmaceutically acceptable salts comprising:
a) a core comprising an effective amount of Pantoprazole or its pharmaceutically acceptable salts, at least a diluent, and an alkaline agent,
b) at least one water-soluble seal coating layer, and
c) at least one enteric coating layer over the seal coat
wherein the said core comprises of disintegrant in the range of from 1-10% w/w and surfactant is in an amount from 0-2% w/w of the core.

Yet another embodiment of the present invention, the delayed release multiparticulate powder for oral suspension of Pantoprazole or its pharmaceutically acceptable salts comprising:
a) a core comprising an effective amount of Pantoprazole or its pharmaceutically acceptable salts, at least a diluent, a surfactant and an alkaline agent,
b) at least one water-soluble seal coating layer, and
c) at least one enteric coating layer over the seal coat and optionally an outer seal coating layer
wherein the said core comprises disintegrant in an amount of less than 14% w/w and/or surfactant in an amount ranging from 0-2% w/w.

In yet another embodiment of the present invention, the solid oral delayed release multiparticulate pharmaceutical composition comprises a pharmacologically effective amount of proton pump inhibitor, preferably Pantoprazole or its pharmaceutically acceptable salt, esters, solvates, polymorphs, enantiomers or mixtures thereof present in an amount of about 30% w/w to about 70% w/w of core, preferably about 50% w/w to about 70% w/w of core, more preferably about 40% w/w to about 60% w/w of the core and a process for preparing the same.

In yet another embodiment of the invention, the solid oral delayed release multiparticulate pharmaceutical composition comprises of a core of a pharmacologically effective amount of Pantoprazole or its pharmaceutically acceptable salt, esters, solvates, polymorphs, enantiomers or mixtures thereof and one or more other excipients, wherein a seal coat of water soluble polymer is present in between the core and the enteric coat, wherein the water-soluble polymer is selected from Hydroxypropyl cellulose, Hydroxypropyl methylcellulose.

In yet another embodiment of the invention, the solid oral delayed release multiparticulate pharmaceutical composition comprises of a core of a pharmacologically effective amount of Pantoprazole or its pharmaceutically acceptable salt, esters, solvates, polymorphs, enantiomers or mixtures thereof and one or more other excipients, wherein the composition is devoid of a seal coat in between the core and the enteric coat. In yet another embodiment of the invention, the solid oral delayed release multiparticulate pharmaceutical composition comprises of about 5 mg to about 240 mg of Pantoprazole or its pharmaceutically acceptable salts, esters, solvates, polymorphs, enantiomers or mixtures thereof.

Another embodiment of the present invention encompasses a solid oral delayed release multiparticulate pharmaceutical compositions comprising Pantoprazole or its pharmaceutically acceptable salts, esters, solvates, polymorphs, enantiomers or mixtures thereof from about 30% w/w to about 70% w/w of the core, preferably about 50% w/w to about 70% w/w of the core, more preferably about 40% w/w to about 60% w/w of the core and a pharmaceutically acceptable excipient selected from at least one of diluent, binder, alkaline agent, glidant, plasticizer and other pharmaceutical excipients. Combination of excipients performing the same function may also be used to achieve desired formulation characteristics.

In yet another embodiment of the present invention, delayed release multiparticulate powder for oral suspension prepared by extrusion spheronization process comprising:
a) a core comprising
about 30% w/w to about 70% w/w of Pantoprazole and its pharmaceutically acceptable salts
about 20% w/w to about 60% w/w of a diluent,
about 0% w/w to about 2% w/w of a surfactant, and
about 2% w/w to about 10% w/w of an alkaline agent,
from 0% w/w to 10% w/w of disintegrant
b) at least one water-soluble seal coating layer and
c) at least one enteric coating layer over the seal coat and optionally an outer seal coating layer.

In another embodiment of the present invention, the solid oral delayed release multiparticulate pharmaceutical composition of the invention is prepared extrusion spheronization technique. Other formulation techniques are also contemplated within the scope of the present invention.

In another embodiment of the present invention, the solid oral delayed release multiparticulate pharmaceutical composition comprising Pantoprazole or its pharmaceutically acceptable salts, esters, solvates, polymorphs, enantiomers or mixtures thereof comprises surfactant in an amount of about 0% w/w to about 4% w/w, preferably in an amount of less than 2%.

In another embodiment, the solid oral delayed release multiparticulate composition comprising Pantoprazole or its pharmaceutically acceptable salts, esters, solvates, polymorphs, enantiomers or mixtures thereof, wherein the particle size of pellets/spheres have an average diameter of about 0.6 mm to about 1.2 mm; preferably from about 0.7 mm to about 1.0 mm.

Another embodiment of the present invention also provides a process for the preparation of a solid oral delayed release multiparticulate pharmaceutical composition of Pantoprazole or its pharmaceutically acceptable salts, esters, solvates, polymorphs, enantiomers or mixtures thereof of, comprising the steps of; (a) dry blending the drug and excipients, (b) wet granulation (aqueous or non-aqueous) of the mass, (c) extrusion through a screen of defined mesh size to compact the wet mass into cylindrical strands, (d) spheronization of cylindrical strands in a spheronizer to convert the cylindrical strands into spheres, (e) seal coating of the spheres, (f) enteric coating of the spheres over the seal coating, and (g) optionally coated with an outer seal coat over the enteric coating layer.

In another embodiment of the present invention, the solid oral delayed release multiparticulates present in the pharmaceutical composition comprising Pantoprazole or its pharmaceutically acceptable salts, esters, solvates, polymorphs, enantiomers or mixtures thereof having a bulk density in the range from 0.72 g/ml to 0.82 g/ml and tapped density in the range from 0.76 g/ml to 0.84 g/ml.

In another embodiment, the solid oral delayed release multiparticulate pharmaceutical composition comprising Pantoprazole or its pharmaceutically acceptable salts, esters, solvates, polymorphs, enantiomers or mixtures thereof, wherein the pellets/spheres exhibited a biphasic dissolution profile, whereby negligible drug release exhibited in an acid stage and substantial drug release exhibited at buffer stage (pH 6.8).

In another embodiment, the solid oral delayed release multiparticulate powder for oral suspension comprising Pantoprazole or its pharmaceutically acceptable salts, esters, solvates, polymorphs, enantiomers or mixtures thereof can be administered by sprinkling the pellets/spheres on teaspoonful full of applesauce or apple juice wherein the composition exhibited stability for at least 10 minutes.

In another embodiment, the solid oral delayed release multiparticulate pharmaceutical composition comprising Pantoprazole or its pharmaceutically acceptable salts, esters, solvates, polymorphs, enantiomers or mixtures thereof are stable at 40° C. and 75% relative humidity at least for a period of about 1 month.

In yet another embodiment, the solid oral delayed release multiparticulate pharmaceutical composition comprising Pantoprazole or its pharmaceutically acceptable salts, esters, solvates, polymorphs, enantiomers or mixtures thereof, are stable at 60° C. for at least 1 week.

In further embodiment, the present invention includes method of using the enteric coated solid oral delayed release multiparticulate pharmaceutical composition comprising pellets/spheres of Pantoprazole or its pharmaceutically acceptable salts, esters, solvates, polymorphs, enantiomers or mixtures thereof in the treatment of Gastroesophageal Reflux Disease (GERD) associated with a history of erosive esophagitis as well as for the treatment of pathological hypersecretory conditions including Zollinger-Ellison Syndrome.

Another embodiment of the present invention includes oral delayed release multiparticulate pharmaceutical compositions comprising Pantoprazole sodium prepared by using dry granulation, dry blending, extrusion spheronization or wet granulation process. Suitable solvents include aqueous or organic solvents. Preferable solvents include, but are not limited to, water, esters such as ethyl acetate; ketones such as acetone; alcohols such as methanol, ethanol, isopropanol, butanol; dichloromethane, chloroform, dimethyl acetamide (DMA), dimethyl sulfoxide (DMSO), ether, diethyl ether and combinations thereof. Preferably, the solvent used during wet mass preparation is water.

In another embodiment of the invention, wet granulation can be performed using Rapid mixer granulator, Fluid bed granulator, Planetary mixer and the like; dry blending can be performed in V-blender or key blender; spheronization can be performed using Fuji Paudal spheronizer or by any other method known in the art.

One embodiment of the invention encompasses a delayed release multiparticulate composition comprising Pantoprazole or a salt thereof and a pharmaceutically acceptable excipient selected from at least one of diluent, binder, disintegrant, surfactant, alkaline agent, and glidant.

In another embodiment of the invention, the solid oral delayed release multiparticulate pharmaceutical composition comprises less than 4% w/w of surfactant, preferably the composition comprises surfactant in an amount of from 0% w/w to 4% w/w, preferably in an amount of 0-2% w/w of the core.

Diluents or fillers are substances which usually provide bulk to the composition. Various useful fillers or diluents include, but are not limited to microcrystalline cellulose, calcium carbonate, calcium phosphate, dibasic anhydrous, calcium phosphate, dibasic dihydrate, calcium phosphate tribasic, calcium sulphate, cellulose powdered, cellulose acetate, compressible sugar, confectioner's sugar, dextrates, dextrose, fructose, lactitol, lactose, magnesium carbonate, magnesium oxide, maltodextrin, maltose, mannitol, polydextrose, simethicone, sodium alginate, sodium chloride, sorbitol, starch, pregelatinized starch, sucrose, trehalose and xylitol, or mixtures thereof. Diluent may constitute from about 10% to about 95% by weight of enteric coated pellets/spheres.

Binders impart cohesiveness to formulation. Various useful binders include, but are not limited to hypromellose, acacia, alginic acid, carbomer, sodium carboxymethylcellulose, dextrin, ethylcellulose, gelatin, glucose, guar gum, hydroxypropylcellulose, maltose, methylcellulose, povidone, copovidone, starch, polyvinyl alcohol or polyethylene oxide, or mixtures thereof. The binder may constitute from about 1% to about 20% by weight of enteric coated pellets/spheres.

Glidants improve flowability and accuracy of dosing. Since the present invention relates to an oral pharmaceutical composition, it is imperative to use glidant(s) to achieve desirable flowability of the active. Glidants used in the composition include, but are not limited to, tribasic calcium phosphate, calcium silicate, cellulose, powdered, colloidal silicon dioxide, magnesium silicate, magnesium trisilicate, starch and talc or mixtures thereof.

Surfactants or surface-active agents improve wettability of the dosage form and/or enhance its dissolution. Surfactants contemplated in the present invention include but are not limited to anionic surfactants, amphoteric surfactants, non-ionic surfactants and macromolecular surfactants. Suitable examples of anionic surfactants include but are not limited to sodium lauryl sulphate, sodium cetyl stearyl sulphate or sodium dioctyl sulphosuccinate etc. Suitable example of an amphoteric surfactant include but is not limited to lecithin. Suitable examples of non-ionic surfactants include but is not limited to cetyl alcohol, stearyl alcohol, cetyl stearyl alcohol, cholesterol, sorbitan fatty acid esters such as sorbitan mono-oleate, polyoxyethylene sorbitan fatty acid esters such as polysorbate 80, polysorbate 20, polyoxyethylene fatty acid glycerides such as macrogol 1000 glycerol monostearate, polyoxyethylene fatty acid esters such as polyoxyl 40 stearate, polyoxyethylene fatty alcohol ethers such as polyoxyl 10 oleyl ether, glycerol fatty acid esters such as glycerol monostearate, commercially available SEPITRAP® 80 or SEPITRAP® 4000 etc. The surfactant may constitute from about 0% to about 5% by weight of enteric coated pellets/spheres.

Disintegrants selected from the group comprising crospovidone, modified starches, croscarmellose sodium, sodium starch glycolate, low substituted Hydroxypropyl cellulose and carboxymethylcellulose calcium. These disintegrants are also known as superdisintegrants. The disintegrant may constitute from about 0% to about 20% by weight of enteric coated pellets/spheres.

Alkaline agent may be used to provide a microenvironment of pH above 7 around the acid labile benzimidazole derivative. Suitable alkaline agents include, but are not limited to, pharmacologically alkali metal, alkaline earth metal or metal salts of weak acids such as sodium carbonate which can be anhydrous or hydrous, calcium carbonate and magnesium carbonate and the pharmacologically hydroxides and oxides of alkaline earth and earth metals such as magnesium hydroxide and magnesium oxide. The alkaline agent may constitute from about 0% to about 10% by weight of enteric coated pellets/spheres.

In another embodiment, the Pantoprazole delayed release multiparticulates of the present invention comprise of a spheroid core comprising about 30% w/w to about 70% w/w of Pantoprazole or its pharmaceutically acceptable salts, esters, solvates, polymorphs, enantiomers or mixtures thereof; at least one diluent present in an amount of less than about 25% w/w or more than about 30% w/w of the core; at least one binder present in an amount of less than about 0.5% w/w or more than about 2% w/w of the core; surfactant optionally present in an amount of less than about 2% w/w of the core; water present in a sufficient amount; an enteric coat on the core comprising a copolymer of methacrylic acid present in an amount of less than about 15% or more than about 45% by weight of the composition; wherein said delayed release multiparticulates have an average diameter of about 0.6 mm to about 1.2 mm. In an embodiment of the present invention, additional Pantoprazole polymorphs may be generated during manufacturing of the formulation, which may reduce the bioavailability of the drug. The present invention includes a solid oral dosage form comprising Pantoprazole sodium sesquihydrate wherein, the polymorphic state is identical in the finished dosage form as the input active ingredient, both at initial and accelerated stability study.

The final formulations may be coated or uncoated. For coating, additional excipients such as film-forming polymers, plasticizers, antiadherents and opacifiers are used.

Various water-soluble polymers are used to form a barrier/seal or film over the core. Examples include but are not limited to cellulose derivatives such as soluble alkyl- or hydroalkylcellulose derivatives such as methylcellulose, hydroxymethyl cellulose, hydroxyethyl cellulose, hydroxypropyl cellulose, hydroxymethylethyl cellulose, hydroxypropyl methylcellulose, sodium carboxymethyl cellulose, etc., acidic cellulose derivatives, dextrins, starches and starch derivatives, polymers based on carbohydrates and derivatives thereof, natural gums such as gum Arabic, xanthans, alginates, polyacrylic acid, polyvinyl alcohol, polyvinyl acetate, polyvinylpyrrolidone, chitosan and derivatives thereof, shellac and derivatives thereof, waxes and fat substances. If desired, the films may contain additional adjuvants for coating such as plasticizers, polishing agents, colorants, pigments, antifoaming agents, opacifiers, antisticking agents, and the like.

Various seal coating polymers include but are not limited to polyvinylpyrrolidone, polyvinyl alcohol, polyethylene glycol, Hydroxypropyl methylcellulose and Hydroxypropyl cellulose.

In another embodiment of the invention, enteric coating polymers suitable for use in the present invention include, but are not limited to, cellulose acetate phthalate (CAP), cellulose acetate trimellitate (CAT), hydroxypropylmethylcellulose phthalate (HPMCP), hydroxypropylmethylcellulose acetate succinate (HPMCAS), hydroxypropylcellulose acetate phthalate (HPCAP), hydroxypropylmethylcellulose acetate phthalate (HPMCAP), ethylcellulose (EC), polyvinyl acetate phthalate methylcellulose acetate phthalate (MCAP) and methacrylic acid copolymers or its derivatives. Methacrylic acid copolymers or its derivatives are available under various trade names such as EUDRAGIT®, Acryl-EZE®, Eastacryl®, and Kollicoat® from Evonik Industries, Colorcon, Eastman Chemical and BASF Fine Chemicals respectively. Preferably, enteric coating polymer suitable for use in the present invention is Eudragit L30D-55.

In another embodiment the present invention includes particle size of free drug particulate form of Pantoprazole or its pharmaceutically acceptable salts, esters, solvates, polymorphs, enantiomers or mixtures thereof, wherein particle diameter at 90% cumulative volume ($d_{90}$) is less than about 100 µm, preferably less than 50 µm. Particle diameter at X % cumulative Particle size reduction can be performed by techniques including but not limited to fluid energy milling, ball milling, colloid milling, roller milling, hammer milling and the like. Particle size and particle size distribution can be measured by techniques such as Laser light scattering (e.g. Malvern Light Scattering), Coulter counter, microscopy and the like.

In yet another embodiment of the invention, the solid oral Pantoprazole delayed release multiparticulates are packaged in a foil, pouch, capsule or other suitable package. The delayed release multiparticulate oral dosage form prepared by the above process can be subjected to in vitro dissolution evaluation according to Test 711 "Dissolution" in the United States Pharmacopoeia 37, United States Pharmacopoeial Convention, Inc., Rockville, Md., 2014 ("USP") to determine the rate at which the active substance is released from the dosage form, and the content of the active substance can be determined in solution by high performance liquid chromatography. When comparing the test and reference products, dissolution profiles should be compared using a similarity factor ($f_2$). The similarity factor is a logarithmic reciprocal square root transformation of the sum of squared error and is a measurement of the similarity in the percent (%) of dissolution between the two curves.

$$f_2 = 50 \cdot \log\{[1+(1/n)\Sigma_{t=1}^{n}(R_t-T_t)^2]^{-0.5} \cdot 100\}$$

Two dissolution profiles are considered similar when the $f_2$ value is equal to or greater than 50.

In another embodiment, solid oral delayed release multiparticulate pharmaceutical composition of the present invention exhibited biphasic drug release whereby after two hours 0 to 5% of Pantoprazole sodium sesquihydrate is released in 750 ml of 0.1 N Hydrochloric Acid (acid stage) solution, sampling at 60, 90 and 120 minutes and not less than 75% of Pantoprazole sodium sesquihydrate is released in 1000 ml 0.05 M Tribasic Sodium Phosphate pH 6.8 buffer (Add 250 ml of 0.2 mM Tribasic Sodium Phosphate after completion of acid stage), sampling at 10, 20, 30, 45 and 60 minutes (Office of Generic Drugs dissolution database) using a USP II apparatus (paddle) at a temperature of 37±0.5° C. and a rotation speed of 100 revolutions per minute. The resultant liquid has been analyzed in UV spectrum at about 289 nm wavelength.

In another embodiment, the solid content of oral delayed release multiparticulate pharmaceutical composition of the present invention does not adhere to the intestinal walls, nasogastric and gastronomy tubes, and pouch material leading to predictable delivery of the drug product to the site of drug release.

Having described the invention with reference to certain preferred embodiments, other embodiments will become apparent to one skilled in the art from consideration of the specification. The invention is further defined by reference to the following examples describing in detail method for the preparation and testing of Pantoprazole pharmaceutical composition. It will be apparent to those skilled in the art that many modifications, both to materials and methods, may be practiced without departing from the scope of the invention. Following examples are set out to illustrate the invention and do not limit the scope of the present invention.

EXAMPLES

The following non-limiting examples are intended to further illustrate certain preferred embodiments of the invention. They are, however not intended to be limiting the scope of the present invention in any way.

Delayed release multiparticulate formulation of Pantoprazole sodium may be prepared by using quantitative formula as given in table 1:

The dosage form as prepared in the above-mentioned process exhibited biphasic drug release as mentioned in above section.

TABLE 1

| S. No. | Ingredients | I | II | III | IV | V | VI |
|---|---|---|---|---|---|---|---|
| | | | | mg/ Sachet | | | |
| | Core | | | | | | |
| 1 | Pantoprazole Sodium Sesquihydrate equivalent to Pantoprazole | 45 | 50 | 52 | 45 | 54 | 60 |
| 2 | Microcrystalline Cellulose (diluent) | 35 | 35 | 31 | 40 | 30 | 22.50 |
| 4 | Polysorbate 80 (surfactant) | 1.00 | — | — | 2.00 | 2.00 | 1.00 |
| 5 | Sodium lauryl sulfate (surfactant) | — | 0.50 | — | — | — | 0.50 |
| 6 | Crospovidone (disintegrant) | 7.5 | — | — | — | — | 5.00 |
| 7 | Hypromellose (binder) | — | — | — | — | — | 5.00 |
| 9 | Hydroxypropyl cellulose | 5 | 8.00 | — | — | 6.00 | — |
| 10 | Povidone | — | — | 5.00 | 3.00 | — | — |
| 11 | Sodium Carbonate | 6.5 | 6.50 | 12.00 | 10.00 | 8.00 | 6.00 |
| 12 | Purified Water | q.s | q.s. | q.s. | q.s. | q.s. | q.s. |
| | Seal Coating | | | | | | |
| 1 | Opadry white | — | 30.000 | — | — | — | 25.00 |
| 2 | Hypromellose | 23.00 | — | 21.00 | 21.00 | 21.00 | — |
| 3 | Povidone | — | — | 1.20 | 1.20 | 1.20 | — |
| 4 | Talc | 7.00 | — | 4.50 | 6.00 | 6.00 | 4.50 |
| 5 | Titanium dioxide | — | — | 3.00 | 1.45 | 1.45 | 2.90 |
| 6 | Polysorbate 80 | — | — | 0.30 | 0.30 | 0.30 | — |
| 7 | Iron oxide | — | — | 0.07 | 0.07 | 0.07 | — |
| 8 | Purified water | q.s | q.s | q.s | q.s | q.s | q.s. |
| | Enteric Coating | | | | | | |
| 1 | Eudragit | 63.4 | 73.00 | 72.50 | 55.00 | 55.00 | 55.25 |
| 2 | Talc | 21 | 11.00 | 11.00 | 11.00 | 10.50 | 10.50 |
| 4 | Triethyl Citrate | 6.00 | 7.00 | 7.50 | 5.50 | 5.50 | 5.00 |
| 5 | Sodium lauryl sulfate | — | 0.14 | 0.14 | 0.11 | 0.11 | 0.12 |
| 6 | Iron oxide | — | 0.018 | 0.018 | 0.014 | 0.014 | 0.014 |
| 7 | Purified Water | q.s. | q.s. | q.s. | q.s. | q.s. | q.s. |
| | Optional Seal Coating | | | | | | |
| 1 | HPMC USP | 1.50 | 1.70 | 1.70 | 1.25 | 1.25 | 1.30 |
| 2 | Talc | 0.4 | 0.50 | 0.50 | 3.00 | 3.00 | 2.50 |
| 3 | Purified Water | q.s. | q.s. | q.s. | q.s. | q.s. | q.s. |
| | Lubrication | | | | | | |
| 1 | Talc | 0.24 | 0.22 | 0.22 | 1.030 | 1.030 | 0.250 |

Preferred Method of Manufacture:
Extrusion-spheronization

Brief Manufacturing Process of Example I

1. Pantoprazole sodium sesquihydrate and pharmaceutical excipients were weighed and dispensed in vessel and mixed well;
2. Sodium carbonate was dissolved in purified water;
3. Mixture of step 1 was granulated with the solution of step 2 to prepare wet mass;
4. Wet mass of step 3 was passed through the extruder-spheronizer; prepared spheroids were then dried;
5. Dried spheroids of step 4 were seal coated with water-soluble polymers and other excipients as mentioned above in Table 1;
6. Seal coated spheroids of step 5 are then coated with Eudragit and; optionally coated with an outer seal coating layer.

Note: Examples II-VI are also prepared by using the same manufacturing process as mentioned in example I with the desired excipients.

The above-mentioned examples I-III of formulation of Pantoprazole delayed-release powder for oral suspension (initial samples) exhibited the in-vitro dissolution profile as shown in Table 2:

TABLE 2

0.1N HCl, 750 ml, USP-II, 100 rpm upto 120 mins followed by 0.05M Tribasic sodium phosphate, pH 6.8, 1000 ml, USP-II, 100 rpm (OGD Media)

| | Batch No. | | | |
|---|---|---|---|---|
| Time point (mins) | PROTONIX ® % Release | Example I % Release | Example II % Release | Example III % Release |
| Acid Stage: 0.1N HCl | | | | |
| 60 | 0 | 1 | 0 | 0 |
| 90 | 0 | 1 | 1 | 0 |
| 120 | 0 | 1 | 4 | 0 |
| Buffer Stage: pH 6.8 | | | | |
| 10 | 30 | 21 | 22 | 21 |
| 20 | 94 | 85 | 84 | 77 |
| 30 | 102 | 94 | 98 | 90 |

TABLE 2-continued 0.1N HCl, 750 ml, USP-II, 100 rpm upto 120 mins followed by 0.05M Tribasic sodium phosphate, pH 6.8, 1000 ml, USP-II, 100 rpm (OGD Media)

| | Batch No. | | | |
|---|---|---|---|---|
| Time point (mins) | PROTONIX ® % Release | Example I % Release | Example II % Release | Example III % Release |
| 45 | 101 | 96 | 101 | 95 |
| 60 | 98 | 97 | 101 | 96 |

The in-vitro dissolution profile of examples I-III exhibit the % drug release as shown in FIG. 1. All the batches exhibited desirable $f_2$ values.

Accelerated stability testing as per the ICH guidelines was conducted on the pellets/spheres prepared in example I-III at temperature/relative humidity of 40° C.±2° C./75%±5% for 1 month. Results in terms of amount of Pantoprazole present in the pellets/spheres of the period of storage were analyzed by validated high performance liquid chromatography method and the same were presented in the Table 3 below:

TABLE 3

| | Description | | Assay (%) by HPLC | | Dissolution (%) by UV | | | |
|---|---|---|---|---|---|---|---|---|
| | | | | | Acid Stage | | Buffer Stage | |
| Example No. | Initial | 40° C./75% RH-1 month | Initial | 40° C./75% RH-1 month | Initial | 40° C./75% RH-1 month | Initial | 40° C./75% RH-1 month |
| Example I | Off-white | Off-white | 100.5 | 99.5 | 0 | 0 | 97 | 100 |
| Example II | Off-white | Off-white | 101.5 | 100.1 | 0 | 1 | 96 | 102 |
| Example III | Off-white | Off-white | 100.5 | 100.3 | 0 | 0 | 98 | 101 |

Figure 2:
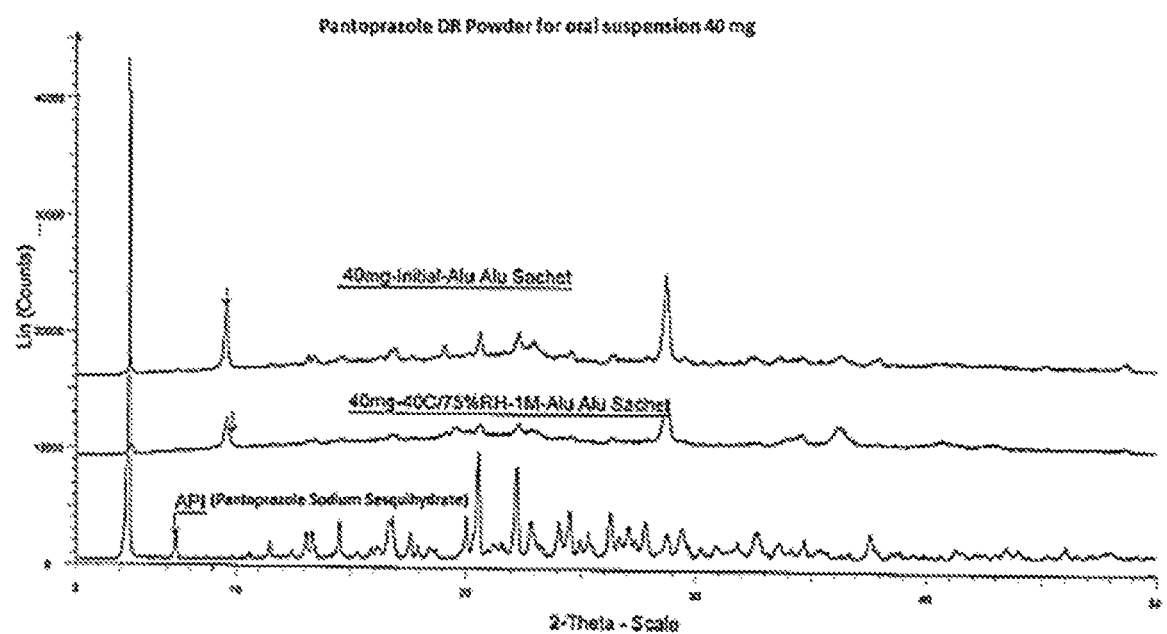
FIG. 2 is a characteristic X-ray diffraction pattern of input API (Pantoprazole sodium sesquihydrate), the packaged multiparticulate powder formulation both at initial and accelerated stability condition.

Further, the XRD data shows that there is no conversion of any polymorphic form as shown in FIG. 2. This figure shows the X-ray diffraction pattern of input API (Pantoprazole sodium sesquihydrate), the multiparticulate powder for oral suspension sachet of Pantoprazole sodium both at initial and accelerated stability conditions.

In view of the above it is clearly evident that the formulation of the invention provide in vitro dissolution of Pantoprazole, which is comparable to Protonix® suspension of Wyeth.

While this invention has been described in detail with reference to certain preferred embodiments, it should be appreciated that the present invention is not limited to those precise embodiments. Rather, in view of the present disclosure, which describes the current best mode for practicing the invention, many modifications and variations would present themselves to those skilled in the art without departing from the scope and spirit of the invention.

The invention claimed is:

1. A delayed release multiparticulate powder for oral suspension comprising:
 a) a core comprising an effective amount of Pantoprazole or its pharmaceutically acceptable salts as the sole active pharmaceutical ingredient, at least one diluent and an alkaline agent,
 b) at least one seal coating layer over the core, and
 c) at least one enteric coating layer over the seal coat,
 wherein the core is free of disintegrant and surfactant and the particle size of the Pantoprazole or its pharmaceutically acceptable salt has a D90 value less than about 100 mm, wherein the powder for oral suspension is not a tablet.

2. The delayed release multiparticulate powder for oral suspension as claimed in claim 1, wherein the multiparticulate powder for oral suspension is prepared by extrusion spheronization process.

3. The delayed release multiparticulate powder for oral suspension as claimed in claim 1,
 wherein the core comprises:
  about 30% w/w to about 70% w/w of said Pantoprazole and its pharmaceutically acceptable salts
  about 20% w/w to about 60% w/w of a diluent,
  about 2% w/w to about 10% w/w of an alkaline agent.

4. A process for the preparation of a delayed release multiparticulate powder for oral suspension as claimed in claim 1, the process comprising the steps of:
 a) dry blending of the pantoprazole or pharmaceutically acceptable salt and excipients,
 b) preparing a solution of an alkaline agent in water,
 c) granulating the solution of step b) with the blend of step a) to form a granulate;
 d) extruding the granulate of step c) to compact the granulate;
 e) drying the compacted granulate;
 f) spheronization of the dried granulate to convert into spheres,
 g) seal coating of the spheres,
 h) enteric coating of the spheres over the seal coating, and
 i) optionally coating with an outer seal coat over the enteric coating layer.

5. The delayed release multiparticulate powder for oral suspension of Pantoprazole or its pharmaceutically acceptable salts as claimed in claim 1, wherein the composition is stable for at least 1 month at 40° C. and 75% relative humidity.

6. The delayed release multiparticulate powder for oral suspension of Pantoprazole as claimed in claim 1, wherein the powder exhibits a drug release comparable to the equivalent dose of a currently marketed oral pantoprazole delayed release powder for oral suspension wherein 0-5% drug is released in 0.1N HCL (750 mL) for 2 hours and at least 75% drug is released within 30 minutes in phosphate buffer (pH 6.8; 1000 ml) using a USP II apparatus at 100 rpm.

7. The delayed release multiparticulate powder for oral suspension as claimed in claim 1, wherein
 the diluent is microcrystalline cellulose, and the alkaline agent is sodium carbonate.

8. The delayed release multiparticulate powder for oral suspension of Pantoprazole as claimed in claim 1, wherein the diluent is selected from the group comprising microcrystalline cellulose, calcium carbonate, calcium phosphate, dibasic anhydrous, calcium phosphate, dibasic dihydrate, calcium phosphate tribasic, calcium sulphate, cellulose powdered, cellulose acetate, compressible sugar, confectioner's sugar, dextrates, dextrose, fructose, lactitol, lactose, magnesium carbonate, magnesium oxide, maltodextrin, maltose, mannitol, polydextrose, simethicone, sodium alginate, sodium chloride, sorbitol, starch, pregelatinized starch, sucrose, trehalose and xylitol, or mixtures thereof.

9. The delayed release multiparticulate powder for oral suspension of Pantoprazole as claimed in claim 1, wherein the alkaline agent is selected from the group comprising alkali metal, alkaline earth metal or metal salts of weak acids such as sodium carbonate which can be anhydrous or hydrous, calcium carbonate and magnesium carbonate and the pharmacologically hydroxides and oxides of alkaline earth and earth metals such as magnesium hydroxide and magnesium oxide.

10. The delayed release multiparticulate powder for oral suspension as claimed in claim 1, wherein the enteric coated cores in the multiparticulate powder have an average diameter of about 0.6 mm to about 1.2 mm.

11. The delayed release multiparticulate powder for oral suspension as claimed in claim 1, wherein the core further comprises microcrystalline cellulose and/or povidone.

12. The delayed release multiparticulate powder for oral suspension as claimed in claim 1, wherein the core comprises pantoprazole sodium sesquihydrate, microcrystalline cellulose, povidone and sodium carbonate.

13. The delayed release multiparticulate powder for oral suspension as claimed in claim 1, wherein the core comprises about 52% (w/w) pantoprazole sodium sesquihydrate, about 31% (w/w) microcrystalline cellulose, about 5% (w/w) povidone and about 12% (w/w) sodium carbonate, wherein the weight percentage is based on the weight of the core.

14. The delayed release multiparticulate powder for oral suspension as claimed in claim 1, wherein the seal coat comprises hypromellose, povidone, talc, and titanium dioxide.

15. The delayed release multiparticulate powder for oral suspension as claimed in claim 7, wherein the seal coat further comprises polysorbate 80 and/or iron oxide.

16. The delayed release multiparticulate powder for oral suspension as claimed in claim 1, wherein the seal coat comprises about 70% (w/w) hypromellose, about 4% (w/w) povidone, about 15% (w/w) talc, and about 10% (w/w) titanium dioxide, wherein the weight percentage is based on the weight of the seal coat.

17. The delayed release multiparticulate powder for oral suspension as claimed in claim 6, wherein the seal coat further comprises about 1% (w/w) polysorbate 80, wherein the weight percentage is based on the weight of the seal coat.

18. The delayed release multiparticulate powder for oral suspension as claimed in claim 1, wherein the enteric coat comprises a methacrylic acid copolymer, talc, triethyl citrate, and sodium lauryl sulfate.

19. The delayed release multiparticulate powder for oral suspension as claimed in claim 1, wherein the enteric coat comprises about 80% (w/w) of a methacrylic acid copolymer, about 12% (w/w) talc, and about 8% (w/w) triethyl citrate, wherein the weight percentage is based on the weight of the enteric coat.

\* \* \* \* \*